(12) United States Patent
Schaffer

(10) Patent No.: US 8,852,158 B1
(45) Date of Patent: Oct. 7, 2014

(54) TEMPORARY INSTRUMENT HOLDER, SHARPS PROTECTOR, PASSING AID AND SAFETY TRANSPORT APPARATUS

(76) Inventor: Michael H. Schaffer, Coral Springs, FL (US)

( * ) Notice: Subject to any disclaimer, the term of this patent is extended or adjusted under 35 U.S.C. 154(b) by 92 days.

(21) Appl. No.: 13/363,515

(22) Filed: Feb. 1, 2012

(51) Int. Cl.
*A61M 5/32* (2006.01)

(52) U.S. Cl.
USPC ........... 604/192; 604/198; 604/263; 206/364; 206/365; 206/366

(58) Field of Classification Search
USPC .......... 604/192, 197, 198, 263; 206/364–366, 206/443; D24/130
See application file for complete search history.

(56) References Cited

U.S. PATENT DOCUMENTS 4,717,386 A * 1/1988 Simmons ...................... 604/192
7,611,012 B2 * 11/2009 Ross .............................. 206/366

\* cited by examiner

*Primary Examiner* — Laura Bouchelle
(74) *Attorney, Agent, or Firm* — Nancy J. Flint, Esq.; Nancy J. Flint, Attorney At Law, P.A.

(57) ABSTRACT

An apparatus for the prevention of sharps injuries, and more particularly sharps injuries caused by needle sticks, scalpel blades, hobby blades and the like, is disclosed. The apparatus comprises an instrument holder, sharps protector, passing aid, and safety transport apparatus that is simple to fabricate and inexpensive, and that accepts sharps of varying size. In particular, the apparatus will accept needles and particularly, bent needles. Further, the apparatus will hold a needle used in multiple injections and which will not dull the needle tip or contaminate the needle tip or the needle.

4 Claims, 26 Drawing Sheets

TEMPORARY INSTRUMENT HOLDER, SHARPS PROTECTOR, PASSING AID AND SAFETY TRANSPORT APPARATUS

FIELD OF THE INVENTION

This invention relates generally to the field of apparatuses for the prevention of sharps injuries, and more particularly sharps injuries caused by needle sticks, scalpel blades, hobby blades and the like.

BACKGROUND OF THE INVENTION

In recent years there has been increased awareness of the need to protect medical personnel from so called "sharps" injuries which are generally referred to as accidental puncturing of the skin caused by needle sticks from syringes needles (epidural, spinal, blood collection, catheter, dialysis, intravenous, ophthalmic, hormonal pen, radiologic) or from accidental cuts from blades, for example, scalpel blades. Sharps injuries can result in transfer of easily treatable infectious diseases as well as much more serious diseases such as HIV and Hepatitis from the patient to the medical personnel. Similarly, sharps injuries can transfer bacteria from the medical theatre to personnel. Damages resulting from sharps injuries can often be expensive in terms of the medical treatment provided to the health care worker as well as loss of work days both to the employer and the employee. The vast majority of sharps injuries will be work related and therefore subject to workman's compensation claims.

Sharps injuries can also be caused outside of the medical arena such as in research laboratories, by hobbyists working on projects and even in funeral homes. In view of the foregoing, it is desirable to provide systems and methods to eliminate or minimize opportunities for sharps injuries to occur.

In response to the foregoing problem, various solutions have been proposed. For example, numerous attempts have been made to devise a needle that retracts back into the barrel. Other systems have been devised wherein a cover is provided to shield the needle or a disposal device is mounted near the operating field that acts as a disposal unit. Another system as shown in U.S. Pat. No. 5,334,173 wherein the needle cap is adhered to a work surface and the used needle is inserted therein after use. Upon completion of the procedure, the entire assembly is then disposed. U.S. Pat. No. 5,498,242 discloses a medical needle sheath and stand for one-handed use. Notwithstanding the foregoing, none of the foregoing methods have been widely adopted in connection with dentistry since needles are often used for multiple injections on the same patient rendering single use disposal devices inadequate, Further, in dentistry it is common for the clinician to bend the needle in order to administer anesthesia.

Notwithstanding the foregoing, most preventable sharps injuries occur when a sharp instrument (scalpel blade, syringe needle) is recapped using the manufacturer provided cap in the case of a needle, is passed between personnel (in the case of a scalpel blade or needle tip) or when a sharps instrument is picked up. Thus, it would be useful to develop a protocol wherein the sharps safety apparatus is capable of being stored and/or moved in a completely protected environment, independent of the manufacturer provided cover.

It is therefore an object of the present invention to provide a temporary instrument holder, sharps protector, passing aid, and safety transport apparatus for use in connection with sharps devices that is an improvement over the prior art.

It is another object of the present invention to provide an instrument holder, sharps protector, passing aid, and safety transport apparatus that is simple to fabricate and inexpensive.

It is yet another object of the present invention to provide an Instrument holder, sharps protector, passing aid, and safety transport apparatus that will accept sharps devices of varying size.

It is still another object of the present invention to provide an improved Instrument holder, sharps protector, passing aid, and safety transport apparatus that will accept needles and particularly, bent needles.

It is another object of the present invention to provide an improve instrument holder, sharps protector, passing aid, and safety transport apparatus that will hold a needle used in multiple injections and which will not dull the needle tip or contaminate the needle.

DETAILED DESCRIPTION OF THE FIGURES

The invention will be described with reference to the accompanying drawings, in which like elements are referenced with like numerals.

DETAILED DESCRIPTION OF THE ILLUSTRATED EMBODIMENTS

Figure 1:
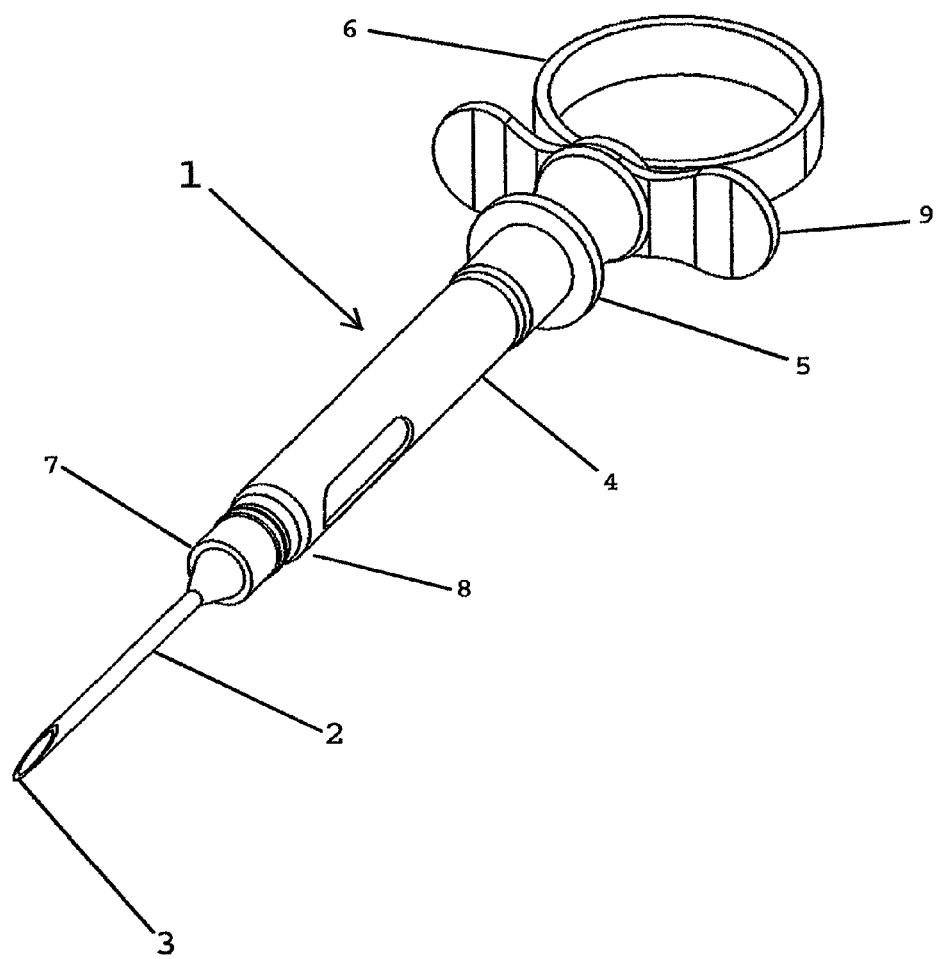
FIG. 1 is a drawing of a common reuseable aspirating syringe and an attached needle.

With reference to the figures, FIG. 1 illustrates a typical reusable aspirating syringe 1 of the type commonly used in dental procedures. Syringe 1 is typically constructed of stainless steel and is designed to be sterilized between patients. Generally aspirating syringes such as that shown in FIG. 1 comprise metal body 4, metal finger flange 9, metal thumb ring 6, and body flange 5. Syringe 1 includes an injury surface comprising a double-ended needle 2 having needle tip 3 is usually connected at distal end 8 to metal body 4 by needle hub 7. These syringes are sturdy, bulky and heavy. However, they remain the preferred tool in the hands of professionals within the dental profession. While the present invention will be described in connection with the use of a dental syringe, it is to be understood that the apparatus of the present invention may be employed with other types of sharps instruments such as scalpel handles and blades, various syringe body/needle combinations, pipettes, hemostats and the like, which have different and varying injury surfaces. Thus, the description which follows is to be understood as a broad teaching disclosure, and not as limiting upon the present invention.

Figure 2:
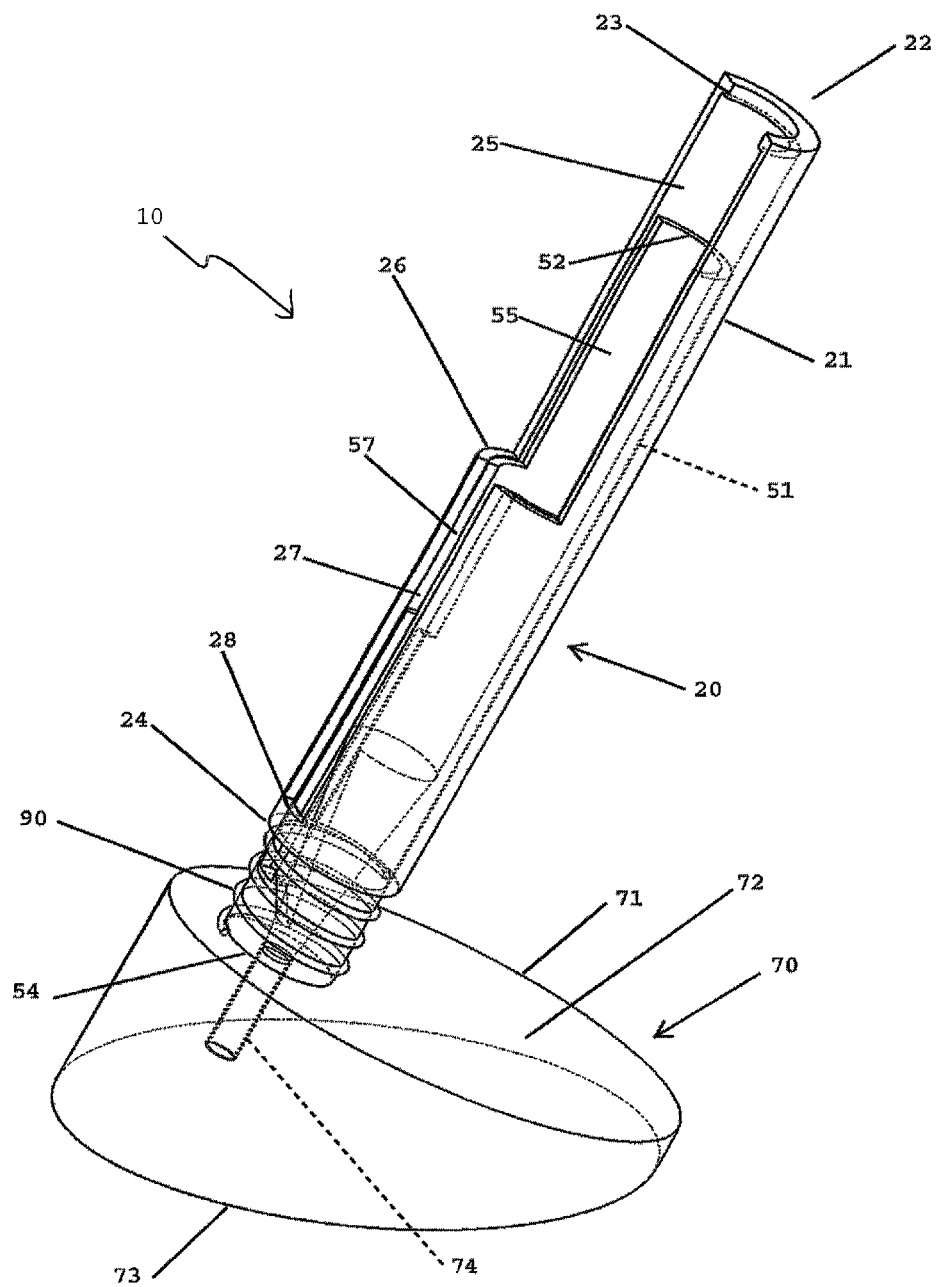
FIG. 2 is a detailed side, oblique view of the sharps safety apparatus according to the present invention.

FIG. 2 illustrates a first preferred embodiment of the sharps safety apparatus of the present invention generally indicated at 10 and comprising an elongate body 20 and a base 70. The elongate body 20 is preferably constructed of two co-axial tubular members 21, 51. First co-axial tubular member 21 defines a first interior cylindrical cavity 25 and comprises a proximal end 22 and distal end 24. First co-axial tubular member 21 further comprises proximal collar 23. Second co-axial tubular member 51 defines a second interior cylindrical cavity 55 and comprises a proximal end 52 and distal end 54, where the outer diameter of second co-axial tubular member 51 is smaller than the inner diameter of first interior cylindrical cavity 25 defined by first co-axial tubular member 21. First co-axial tubular member 21 is slideably disposed upon second co-axial tubular member 51 so that it moves between a first proximal position to a second distal position. Second co-axial tubular member 51 is fixed within base 70 at a preferred angle to a supporting surface (usually a planar tabletop) upon which sharps safety device 10 is placed. First and second co-axial tubular members 21, 51 are held in a co-axial relationship even though there are side openings or slits 27, 57 through which an object may be inserted into interior cylindrical cavity 55 defined by second co-axial tubular member 51. First and second co-axial tubular members 21, 51 may further comprise a shoulder 26 wherein side openings 27, 57 are larger toward the proximal ends of co-axial tubular members 21, 51 than at distal ends of co-axial tubular members 21, 51. First and second co-axial tubular members 21, 51 further comprise first and second conical-shaped distal ends 28, 58, respectively. When sharps safety apparatus 10 is not in use, first co-axial tubular member 21 is biased to a proximal position by compression spring 90 between base 70 and distal end 24 of first co-axial tubular member 21. Collar 23 of first co-axial tubular member 21 has an inner diameter smaller than the outer diameter of second co-axial tubular member 51 which restricts the movement of first co-axial tubular member 21 towards base 70. Sharps safety device further comprises base orifice 54 where the outer diameter of compression spring 90 is greater than the outer diameter of base orifice 54 such that compression spring 90 remains atop base 70. Base 70 comprises angled proximal face 72, distal face 73 and a recess 74 extending into base 70 from proximal face 72.

Figure 3:
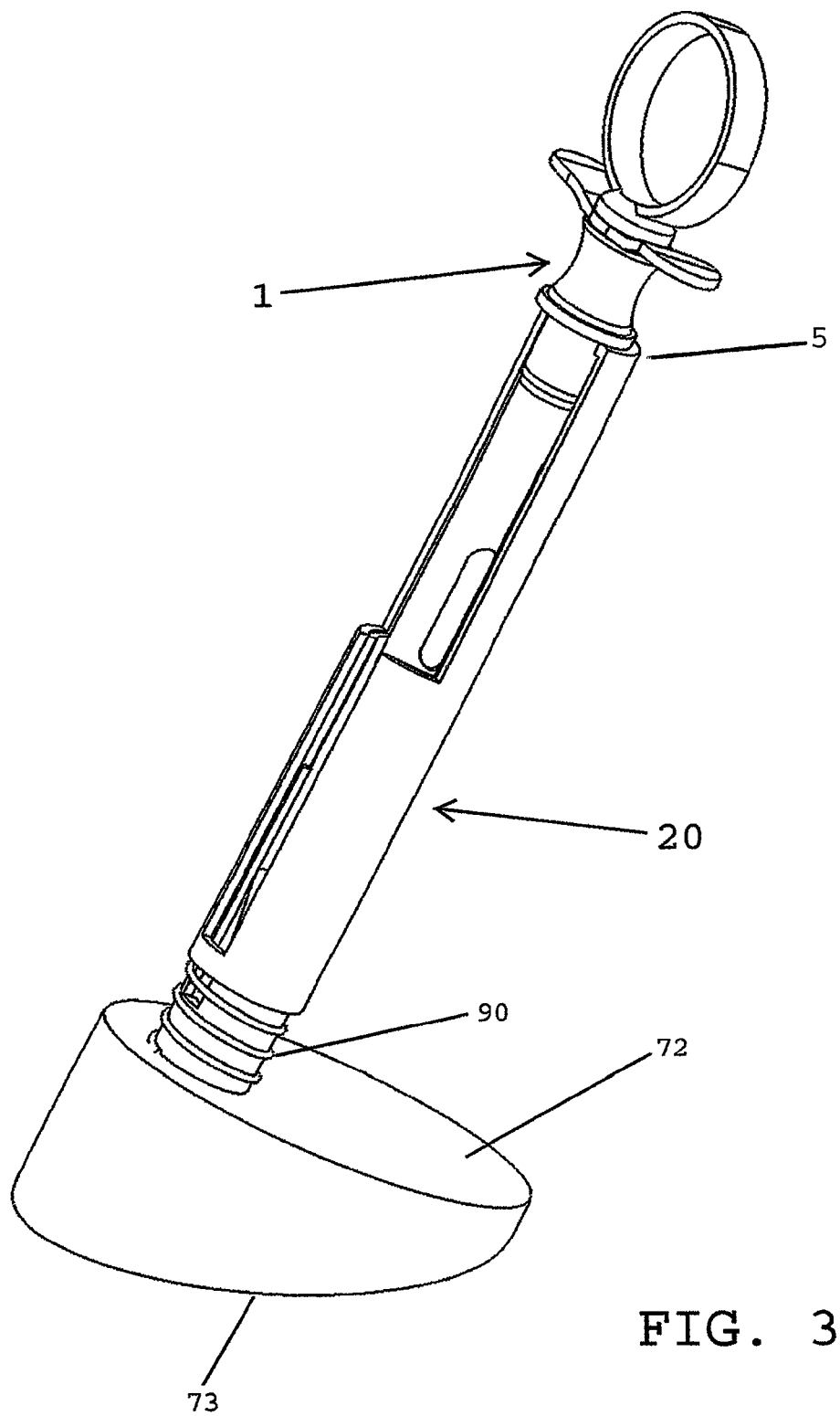
FIG. 3 is an oblique view of the sharps safety apparatus according to the present invention holding a reusable aspirating syringe and an attached needle.
Figure 4:
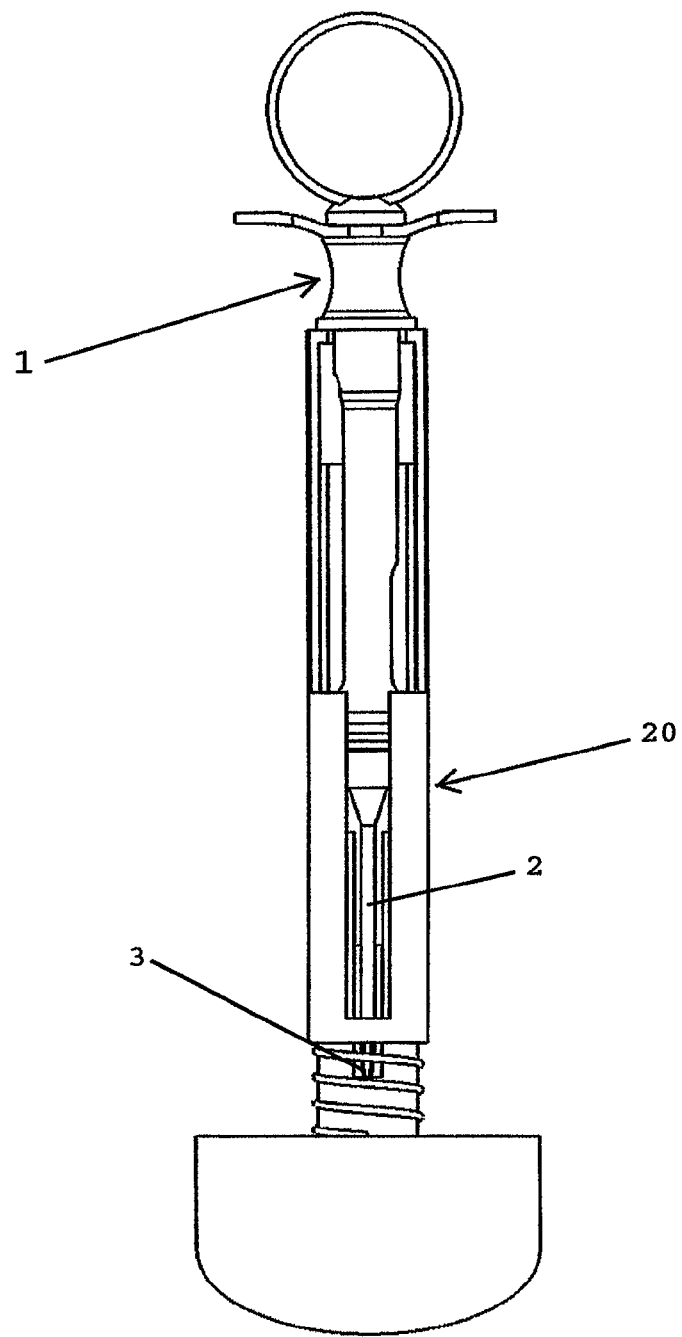
FIG. 4 is a front view of the sharps safety apparatus according to the present invention holding a reusable aspirating syringe and an attached needle.
Figure 5:
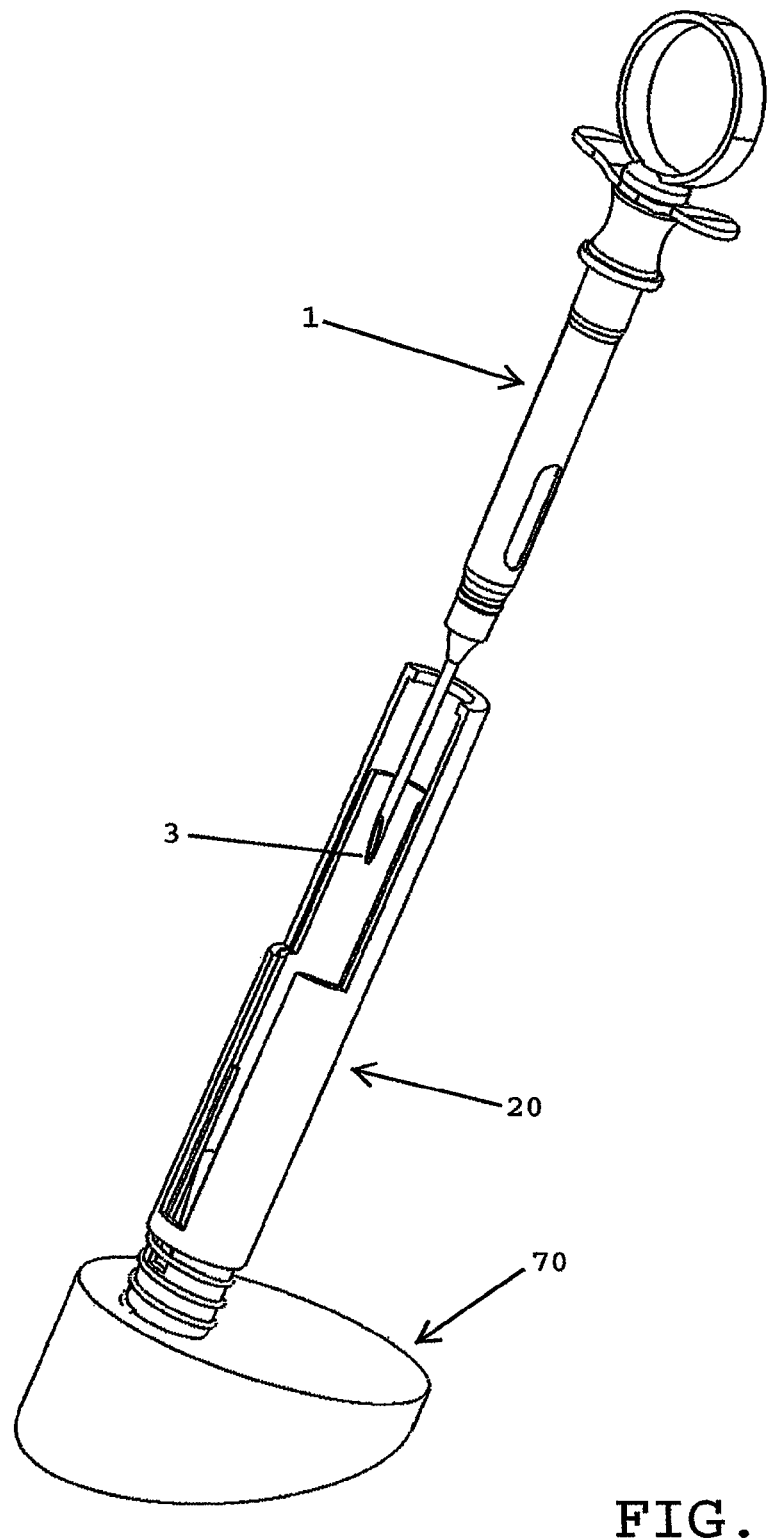
FIG. 5 is an oblique view of the sharps safety, apparatus according to the present invention illustrating placement of a reusable aspirating syringe and an attached needle.
Figure 6:
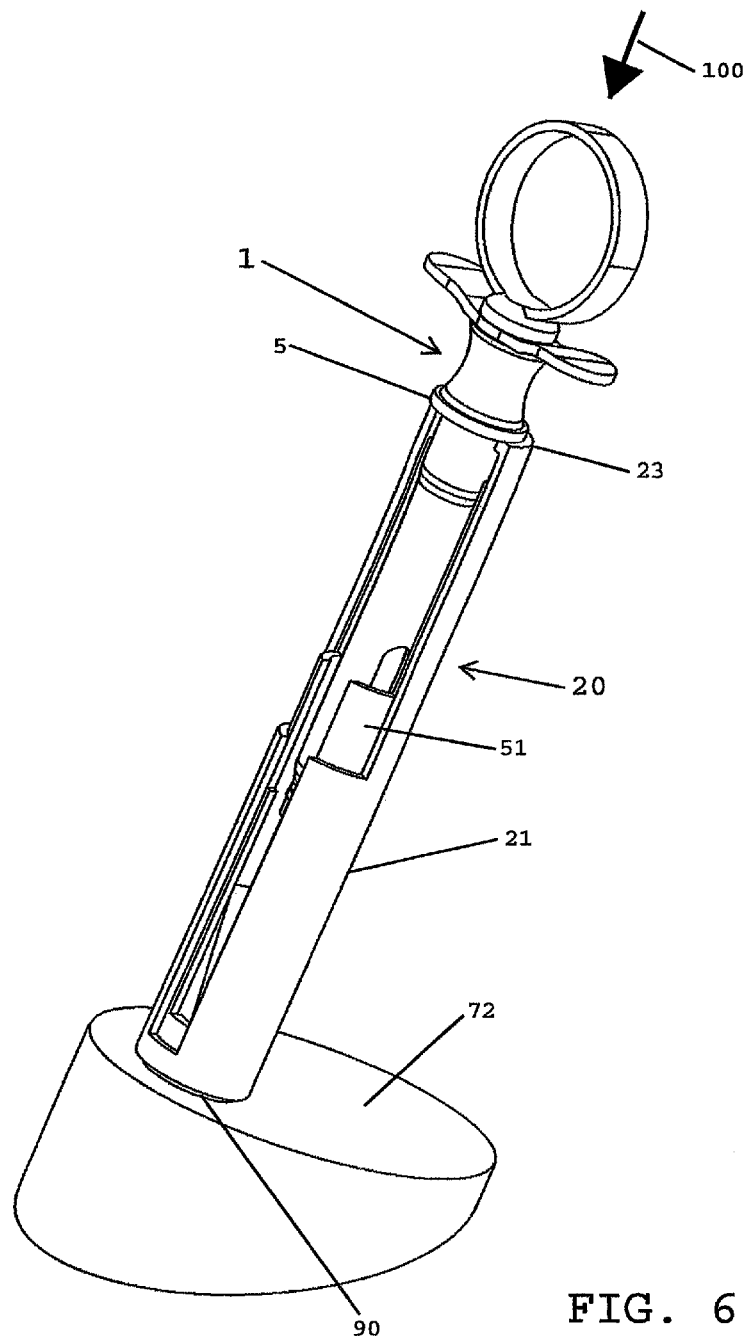
FIG. 6 is an oblique view of the sharps safety apparatus according to the present invention illustrating the spring compression phase.
Figure 7:
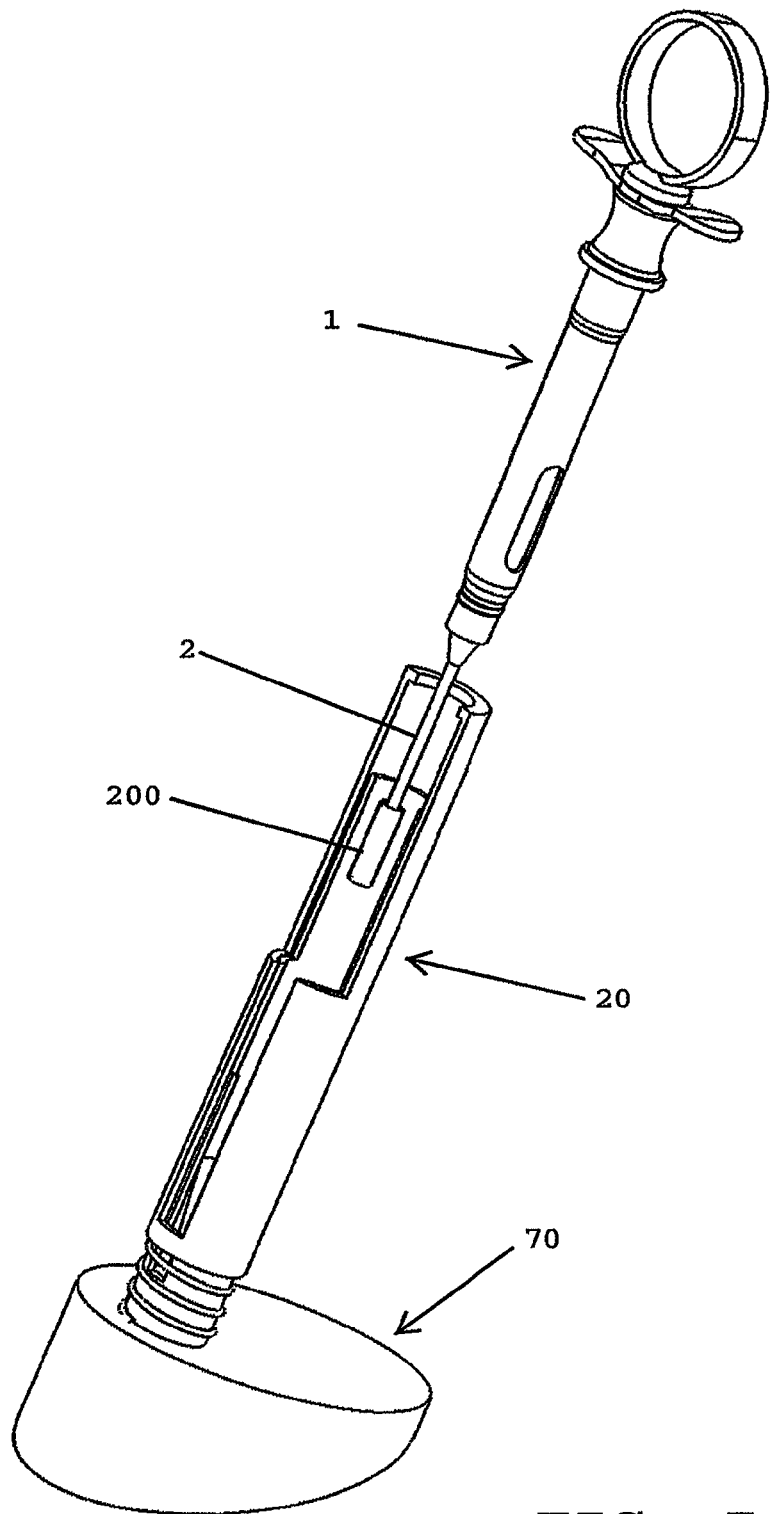
FIG. 7 is an oblique view of the sharps safety apparatus according to the present invention illustrating the release phase.
Figure 8:
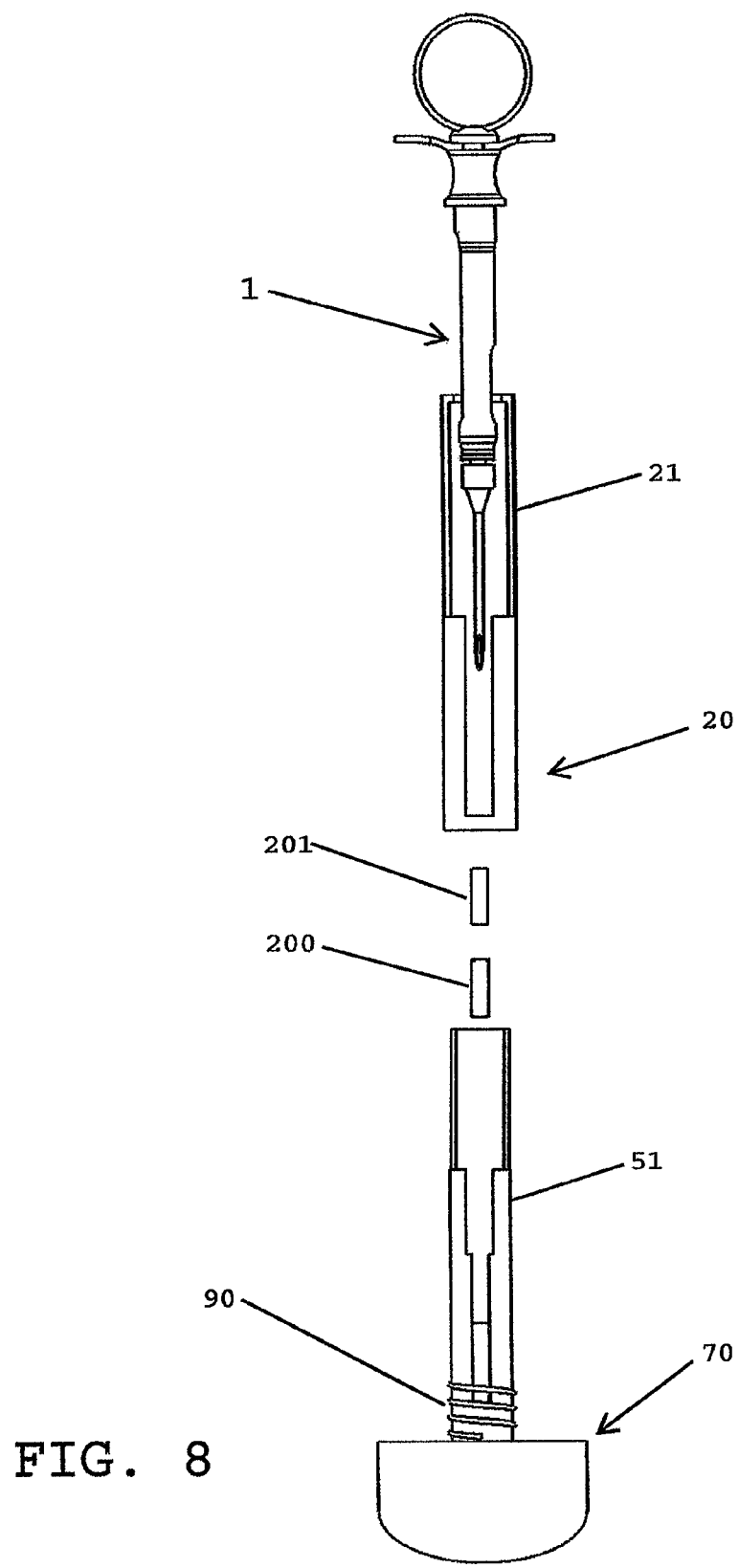
FIG. 8 is an exploded front view of the sharps safety apparatus according to the present invention.
Figure 9:
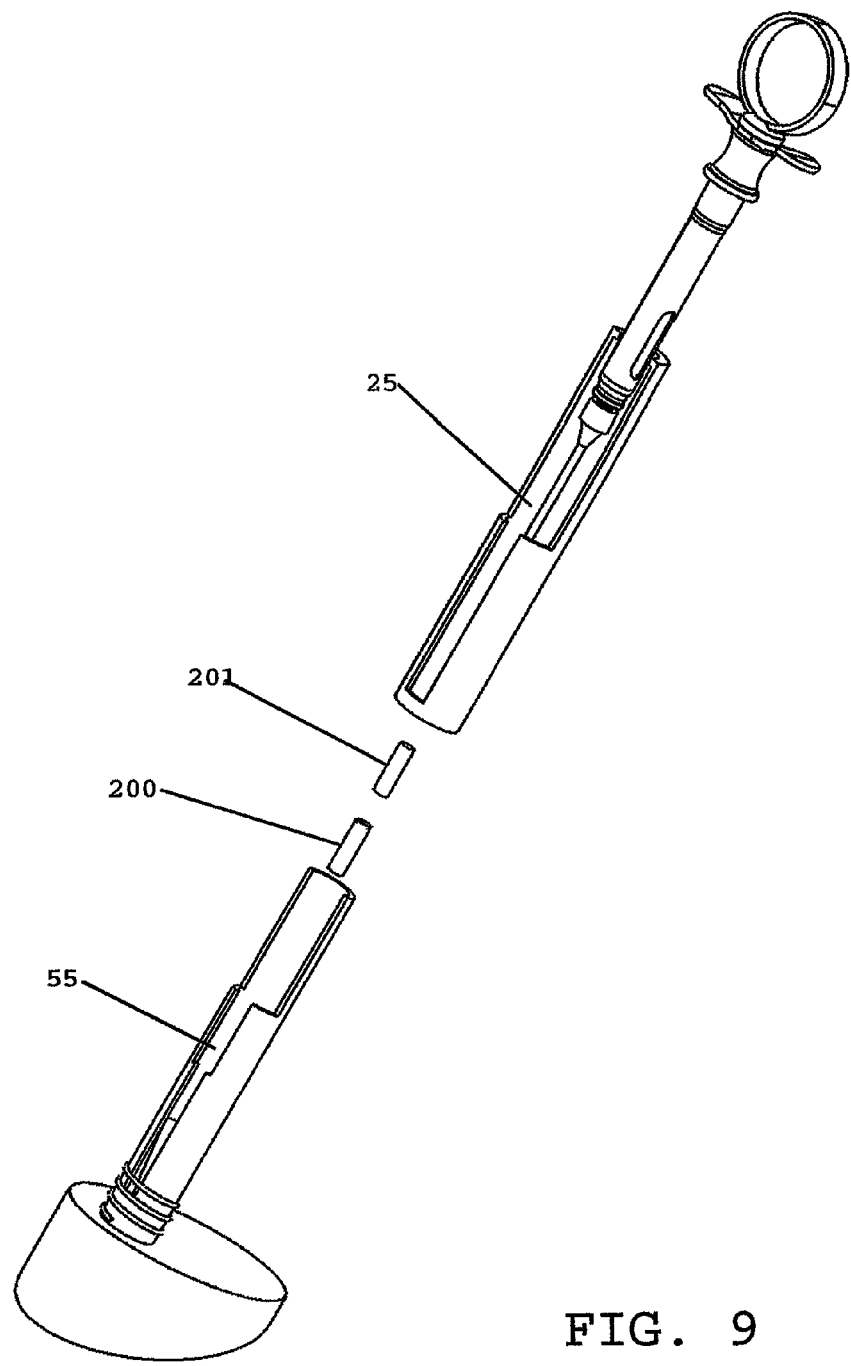
FIG. 9 is an exploded oblique view of the sharps safety apparatus according to the present invention.
Figure 10:
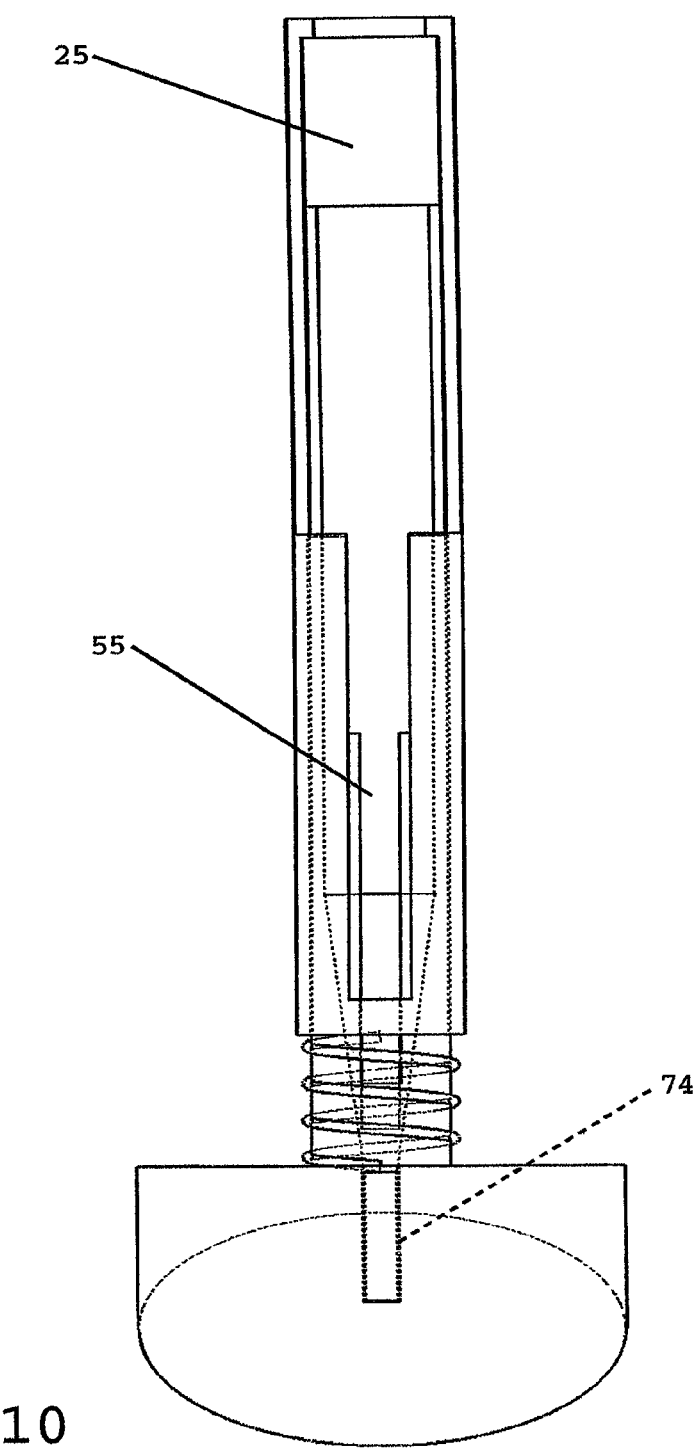
FIG. 10 is a detailed front view of the sharps safety apparatus according to the present invention.

With reference to FIGS. 3, 4 and 5, the present invention may be used to temporarily hold a device having a sharp or contaminated distal point (usually, a syringe and attached medial needle). As illustrated in the figures, a reusable, aspirating syringe 1 may be placed within second interior cylindrical cavity 55 defined by second co-axial tubular member 51 between injections or for transport. Base 70 is sized and configured to maintain an upright position with syringe 1 in place due to the angle of proximal face 72 with respect to distal face 73. In addition, base 70 should be weighted or include an attachment member such as a suction cup, hook and loop fastener, clamp, adhesive or the like. It will be noted that the diameter of first co-axial tubular member 21 is smaller than the outer diameter of body flange 5 of syringe 1 so that syringe 1 will not fall into the second interior cylindrical cavity 55 defined by second co-axial tubular member 51. Further, it will be noted that the length of each of first and second co-axial tubular members 21, 51 is longer than the distance from needle tip 3 to the underside of body flange 5 of syringe 1 which prevents damage to needle tip 3 as the result of striking the bottom of capture member 200, contained within recess 74 in base 70. This aspect of the present invention enables the safe storage and transport of bent needles often used by dental practitioners, not offered by other systems. Thus, it will be seen that syringe 1 may be placed within the present invention, safely stored and easily removed for repeated use, without risk of contamination or damage to needle tip 3 or needle shaft 2.

Figure 17:
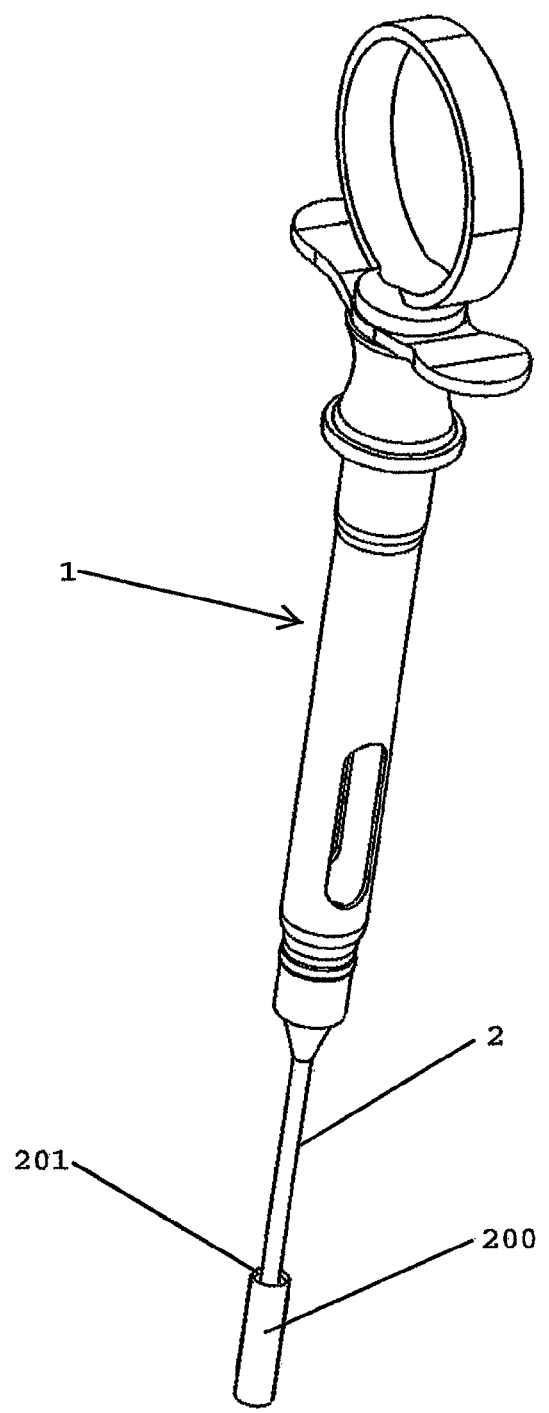
FIG. 17 illustrates an aspirating syringe withdrawn from the sharps safety apparatus and showing the needle tip protected within an attached capture member.
Figure 18:
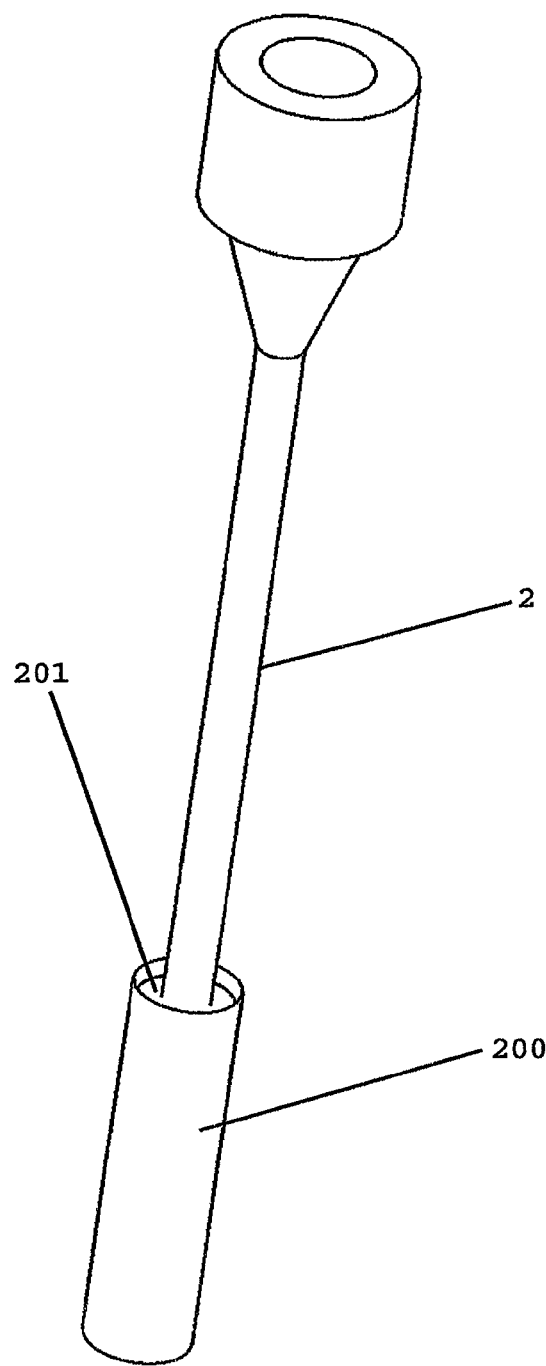
FIG. 18 illustrates an aspirating syringe with the needle detached and with the needle tip embedded in the capture member.

Referring now to FIGS. 6-12 when the user has completed procedures using syringe 1, downward force 100 is placed on syringe 1 so that it is urged distally within the second interior cylindrical cavity 55 defined by second co-axial tubular member 51 of elongate body 20. First co-axial tubular member 21 slides downward over second co-axial tubular member 51 to a forward, distal position, and distal end 24 of first co-axial tubular member 21 mates with compression spring 90, compressing compression spring 90 against base 70 and creating a distal pressure. Needle tip 3 of syringe 1 is urged into capture member 200, which is removably disposed within recess 74 in base 70 and preferably comprises an essentially needle impermeable material such as a metal or hard plastic. Capture member 200 is filled at the distal end with a needle gripping material 201 such as wax, nylons, polyesters, adhesives, or the like. When the downward force on syringe 1 is released, the distal pressure created by compression of compression spring 90 is released and first co-axial tubular member 21 slides over second co-axial tubular member 51 to return to the first proximal position under the influence of compression spring 90. Capture member 200 is lifted out of recess 74 by the upward movement of first co-axial tubular member 21 due to capture of needle tip 3 within needle gripping material 201. As shown in FIGS. 17 and 18, syringe 1 having covered needle 2 is now safe to handle or transport.

Figure 13:
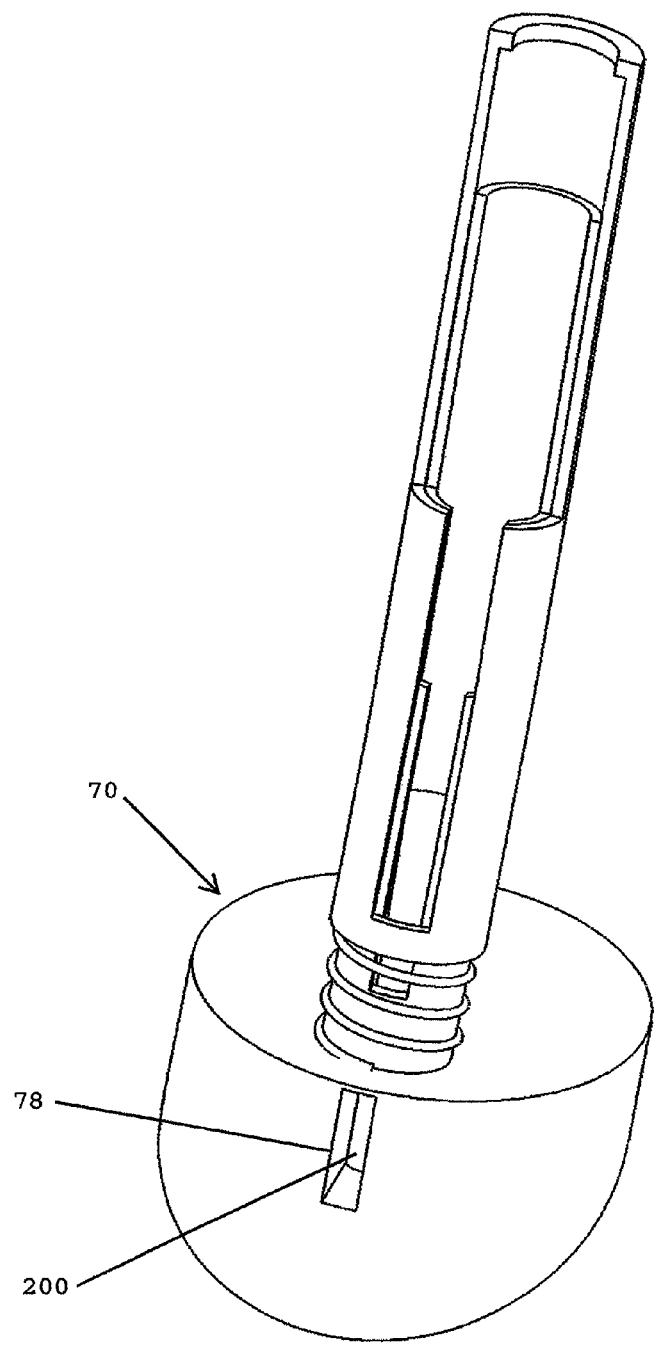
FIG. 13 is an oblique view of the sharps safety apparatus according to the present invention illustrating a feature for multiple inserts.

FIG. 13 depicts an alternative embodiment wherein the sharps safety apparatus comprises a feature for the insertion of capture member 200. Base 70 comprises a slot 78 through which capture member 200 can be inserted into recess 74. The refilling procedure may be by "hand filling" or may include a device for dispensing individual needle capture members from a holding chamber (not shown) into base recess 74.

Figure 11:
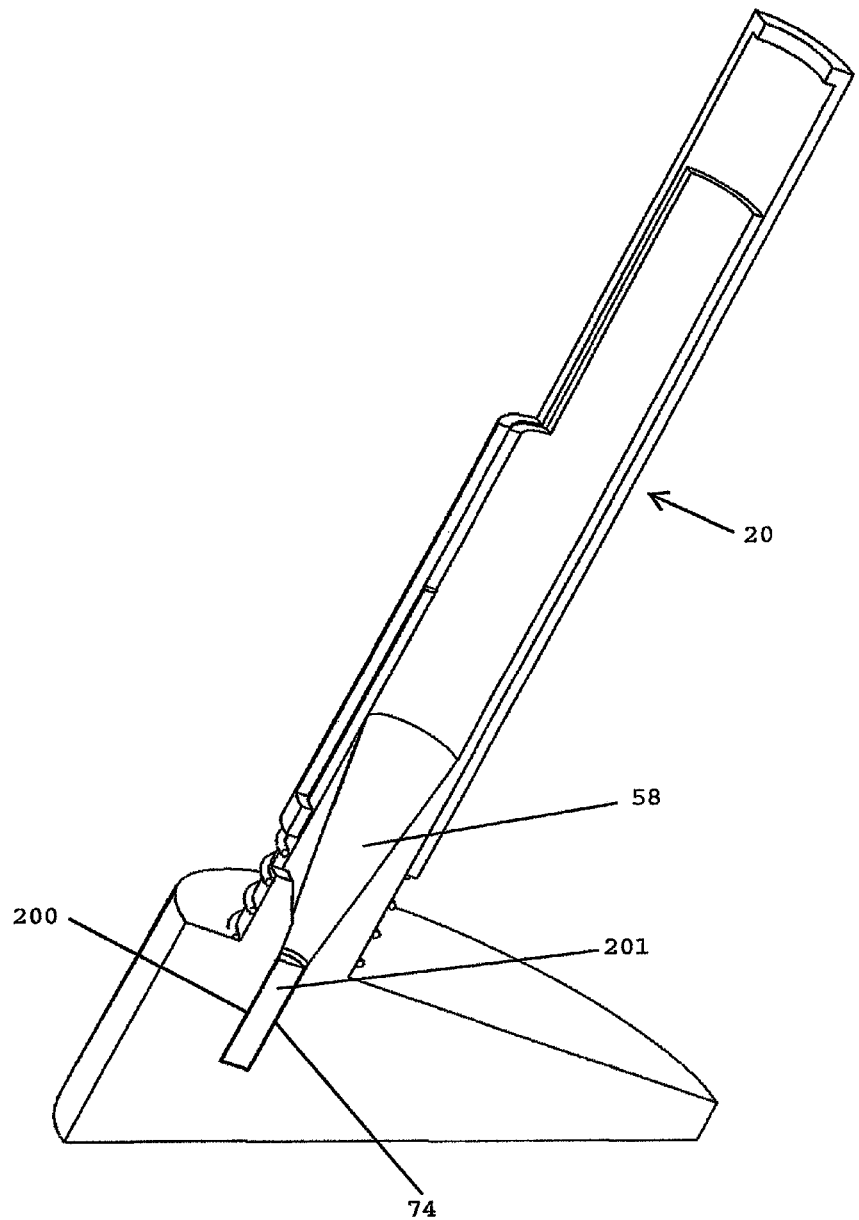
FIG. 11 is an oblique section view of the sharps safety apparatus according to the present invention.
Figure 12:
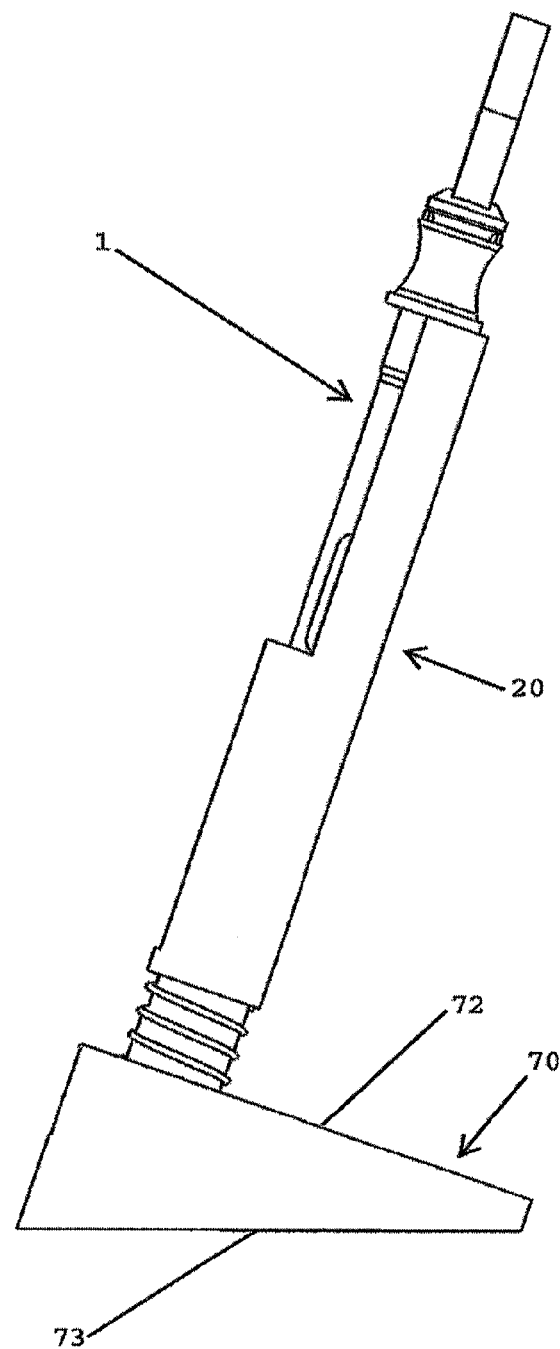
FIG. 12 is a side view of the sharps safety apparatus according to the present invention.
Figure 14:
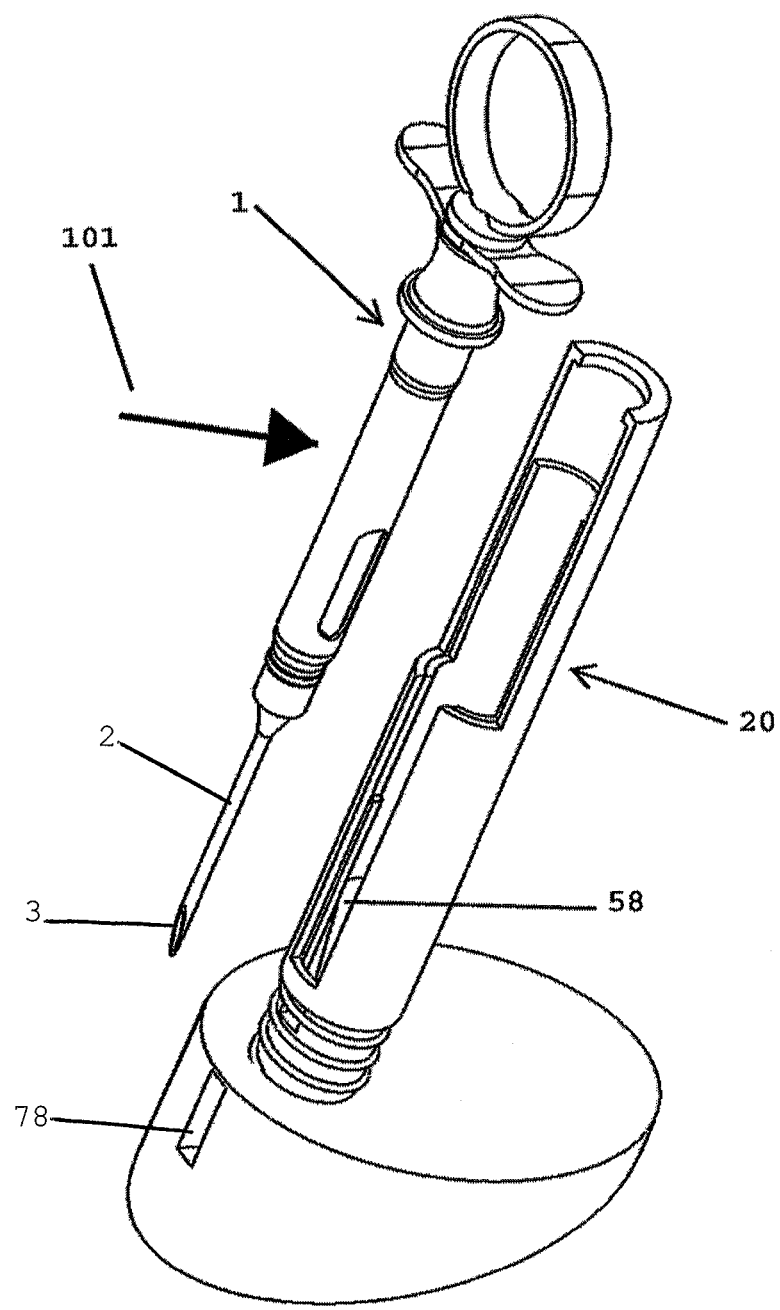
FIG. 14 is a perspective view, taken from above and illustrating a method of introducing an aspirating syringe into the sharps safety apparatus according to the method of the present invention.
Figure 15:
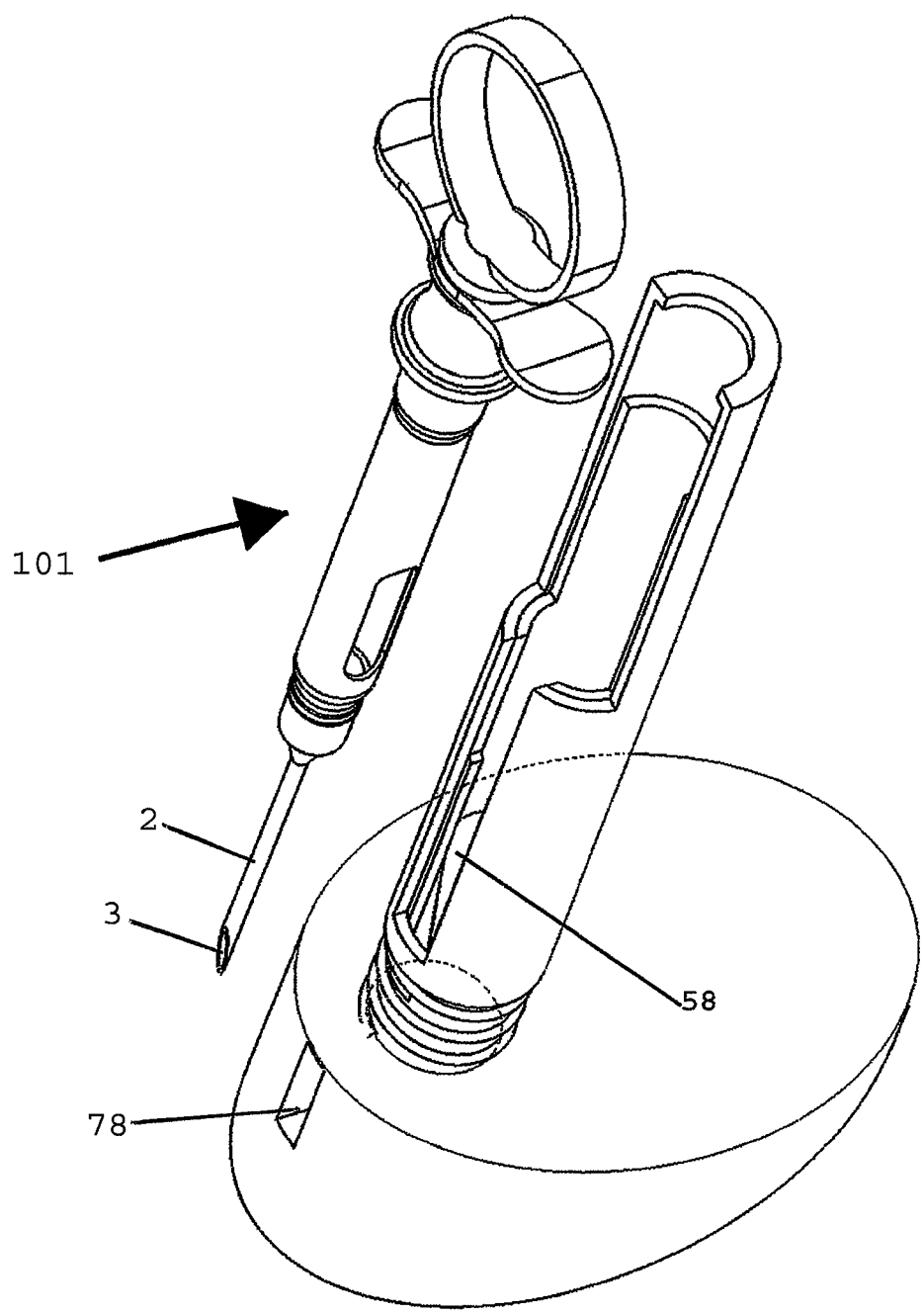
FIG. 15 illustrates further a method of introducing an aspirating syringe into the sharps safety apparatus according to the method of the present invention.
Figure 16:
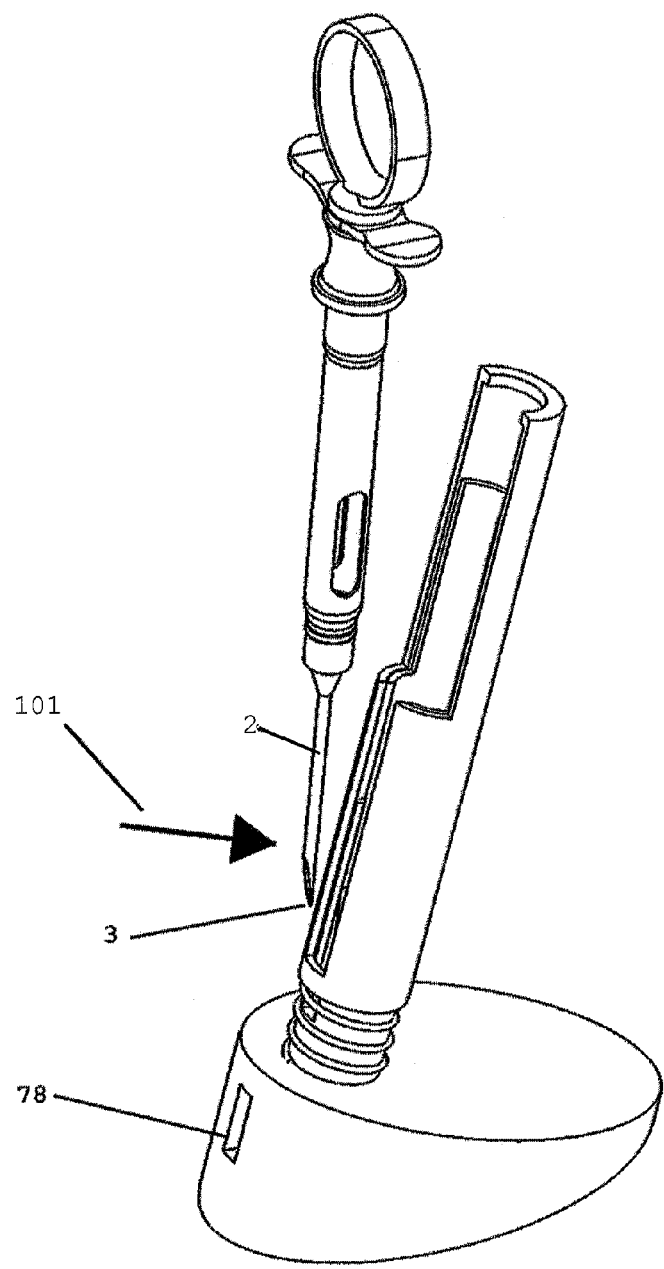
FIG. 16 illustrates a preferred method of introducing an aspirating syringe into the sharps safety apparatus according to the method of the present invention.

FIGS. 14-16 illustrate a method for placing syringe 1 having a delicate distal needle tip or point 3 wherein syringe 1 and needle 2 are presented to the sharps safety apparatus from a frontal 101, or side position. According to the method of the invention, needle tip 3 may be placed into second cylindrical cavity 55 defined by second co-axial tubular member 51 as shown in FIG. 11 until its downward movement is stopped at second conical shaped distal end 58. Placement of syringe 1 and needle 2 within second cylindrical cavity 55 defined by second co-axial tubular member 51 should be undertaken to avoid damaging the extremely delicate distal point 3 of needle 2. This is especially important particularly where multiple injections are indicated with syringe 1. If needle tip 3 is blunted, or needle shaft 2 is bent, it may cause pain or misdirected injection.

FIGS. 17 and 18 illustrate syringe 1 after it has been withdrawn from the sharps safety apparatus 1 and showing needle tip 3 protected within attached capture member 200 by needle gripping material 201.

Figure 19:
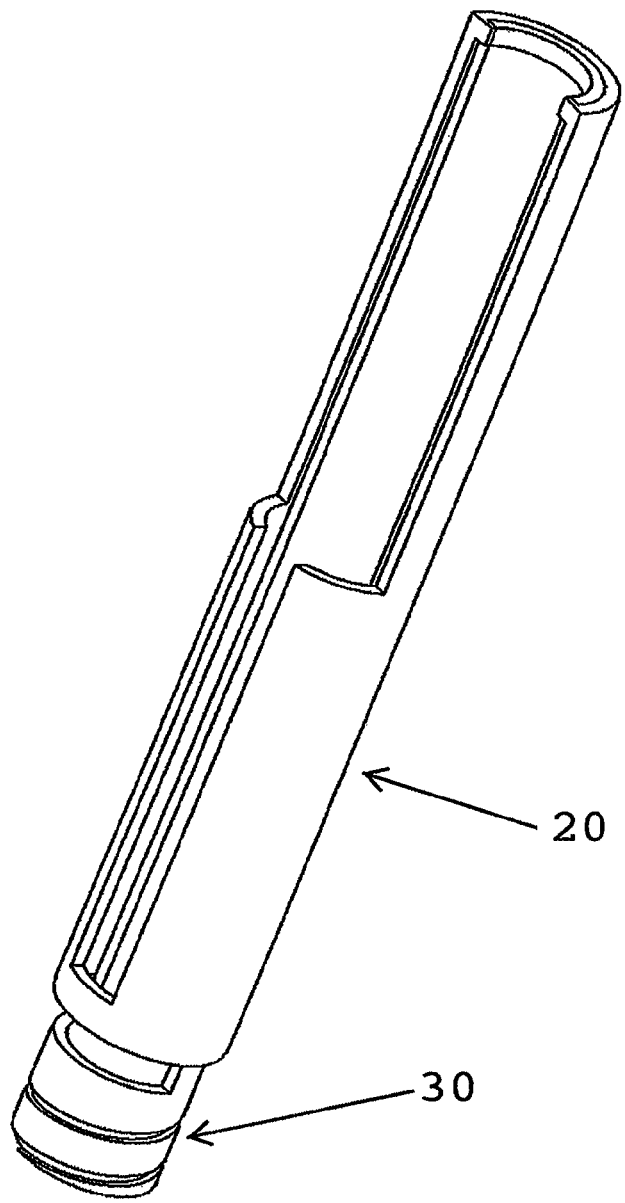
FIG. 19 illustrates an embodiment of the sharps safety apparatus according to the present invention where the co-axial tubular members are detachable from the base.
Figure 20:
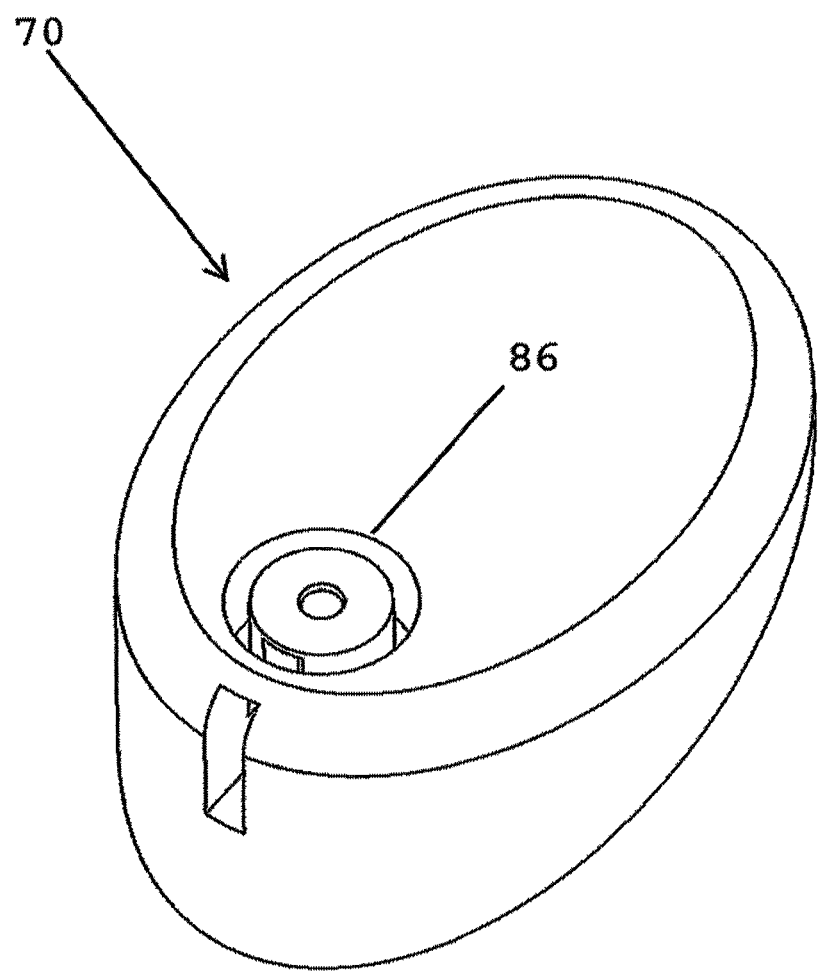
FIG. 20 illustrates an embodiment of the sharps safety apparatus according to the present invention having a disposable base and further containing a plurality of shielding members.

Referring now to FIGS. 19 and 20, the illustrated embodiment contemplates that base 70 may be separated from co-axial tubular members 21, 51 for sterilization at orifice 86. Base 70 may include a disposable member or cartridge system (not shown) that holds a plurality of capture members 200.

Figure 21:
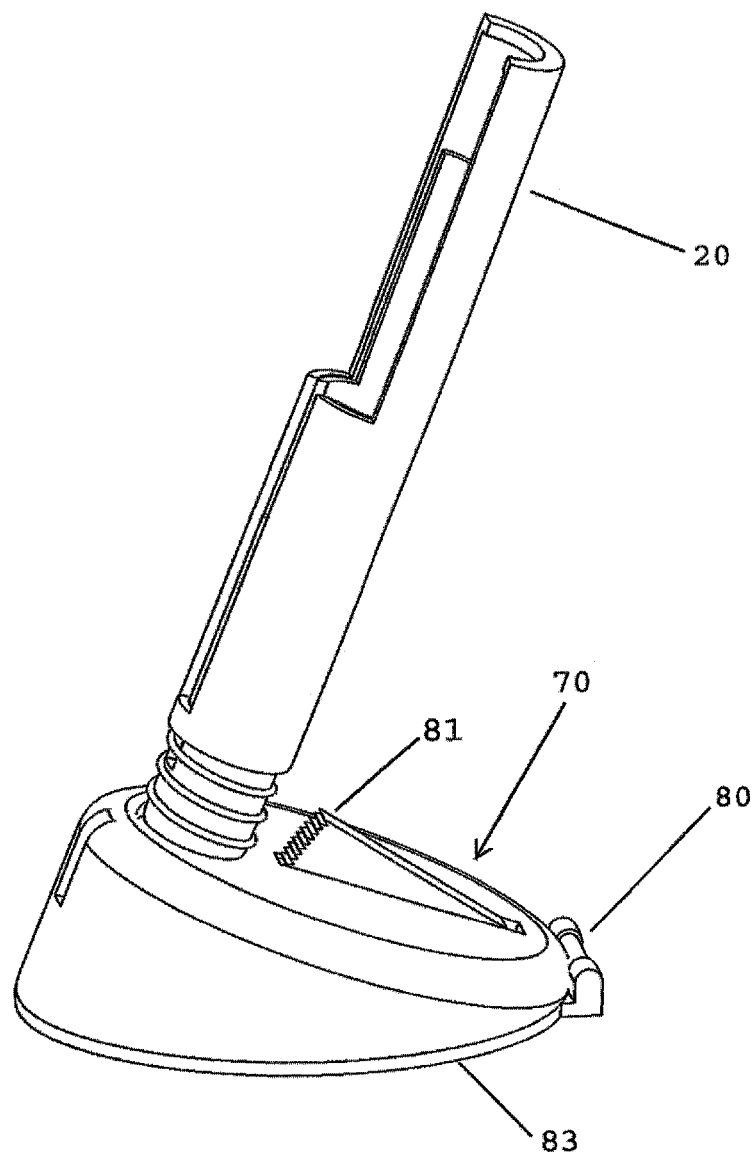
FIG. 21 illustrates an embodiment of the sharps safety apparatus according to the present invention having angularly adjustable co-axial tubular members.
Figure 22:
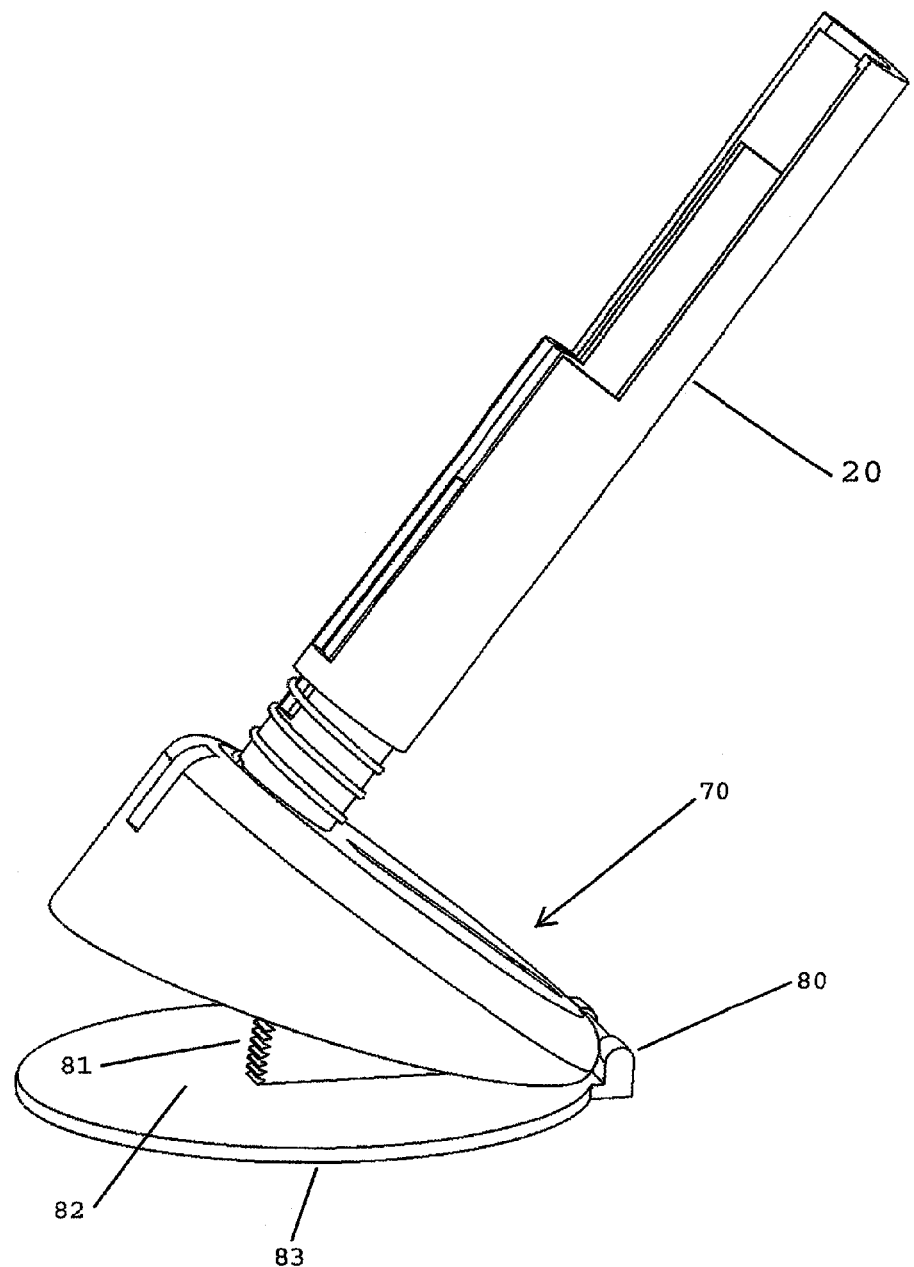
FIG. 22 illustrates an embodiment of the sharps safety apparatus according to the present invention having angularly adjustable co-axial tubular members.
Figure 23:
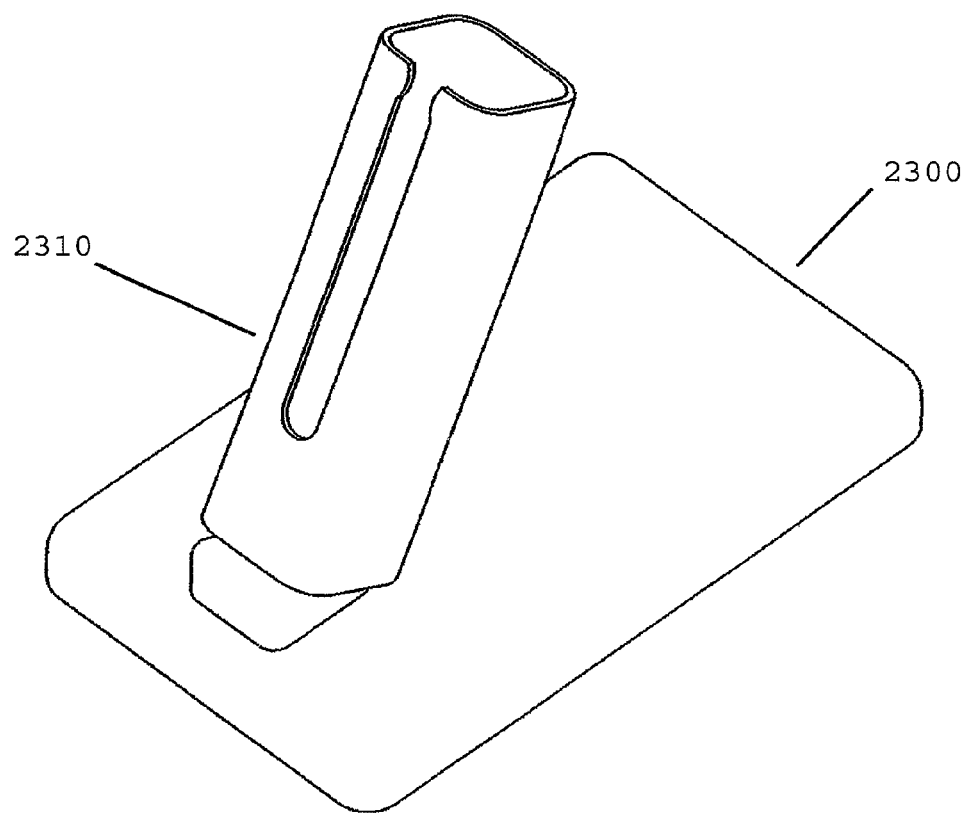
FIG. 23 is a perspective view, taken from above and illustrating an alternate, simplified embodiment of the present invention.
Figure 24:
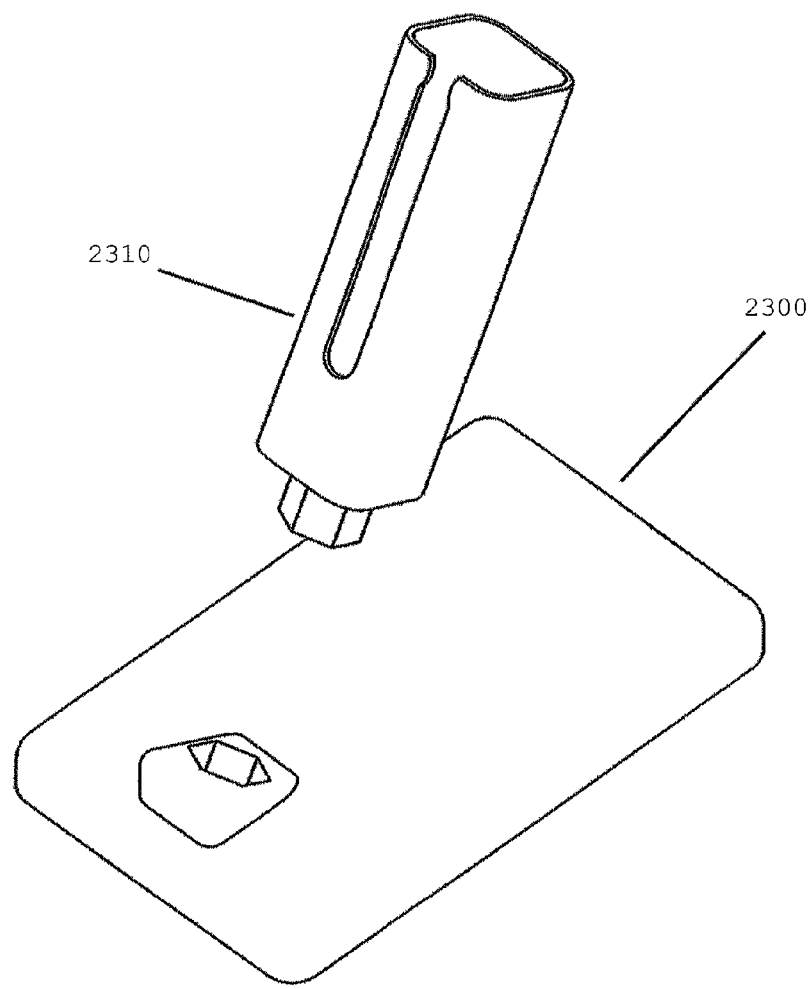
FIG. 24 is an oblique view of the embodiment of FIG. 23 of the sharps safety apparatus according to the present invention illustrating showing the containment portion separated from the base portion.
Figure 25:
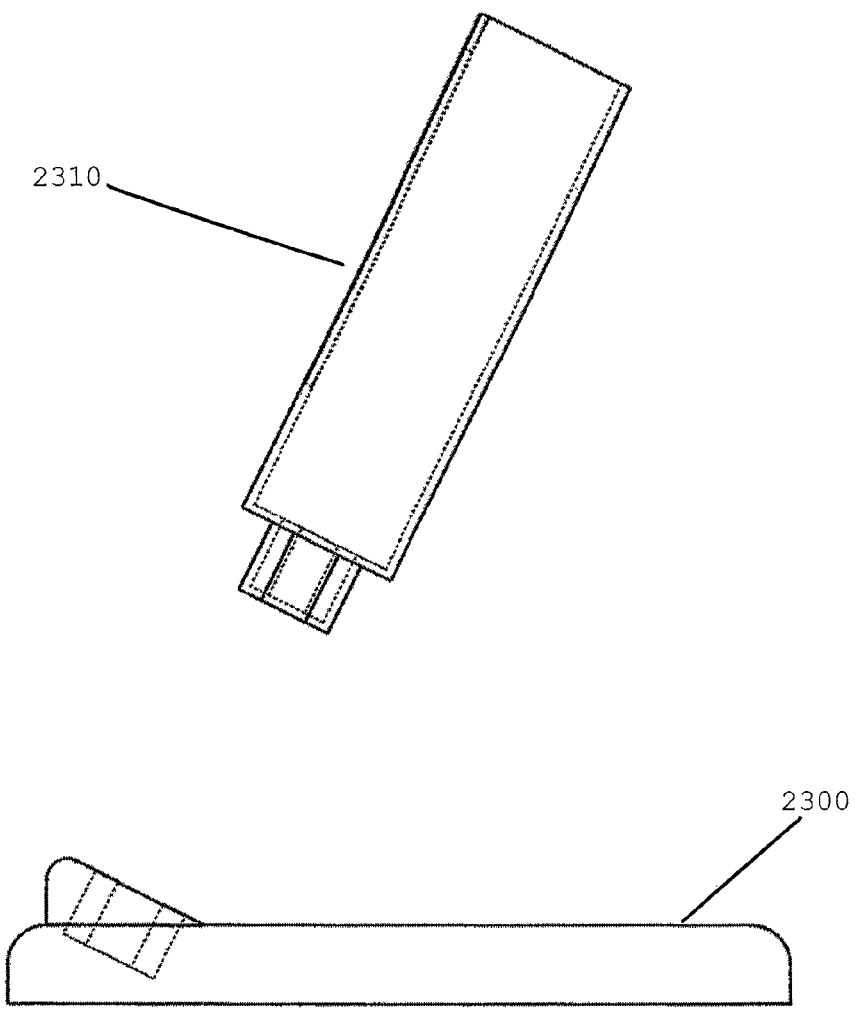
FIG. 25 is side view of the embodiment of FIG. 23 of the sharps safety apparatus according to the present invention illustrating showing the containment portion separated from the base portion.
Figure 26:
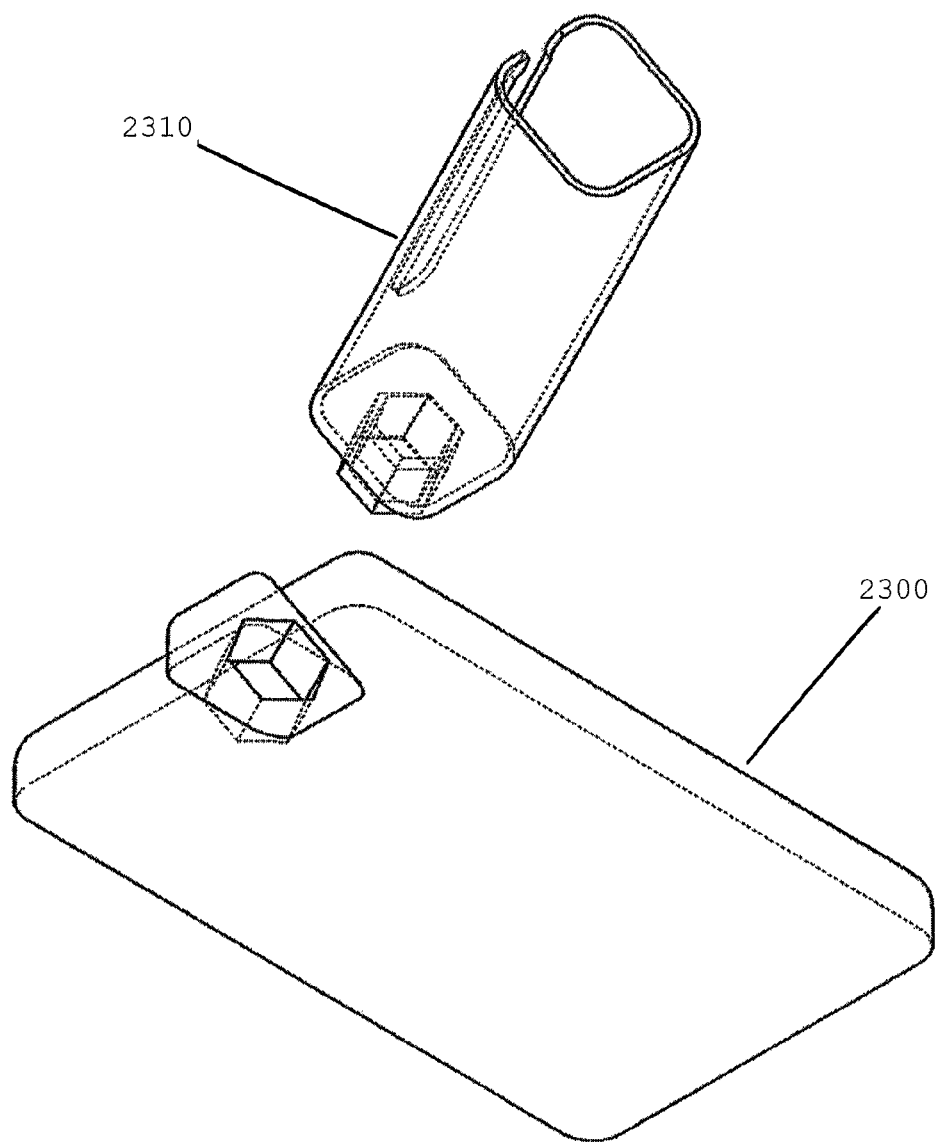
FIG. 26 is an oblique, detailed, view of the embodiment of FIG. 23 of the sharps safety apparatus according to the present invention as viewed from a user point-of-view.

FIGS. 21 and 22 illustrate an embodiment that includes means for angularly adjusting base 70 relative to its supporting surface. In the illustrated embodiment, base 70 is in a hinged relationship with base plate 83 so that it is rotatable about the axis of a hinge 80. A ratchet or detente member 81 is configured to releasably maintain a preferred angular position between base 70 and base plate 83. Alternatively, a pivot point (not shown) may be provided between base 70 and elongated body 20.

FIGS. 23-26 illustrate an alternate embodiment of the present invention. As shown, the embodiment comprises base 2300 and tubular member 2310 detachably connected thereto. While not illustrated, the preferred method of connecting base 2300 and tubular member 2310 is via threads or guided slip-fit, well known to those skilled in the art. Tubular member 2310 is constructed and arranged to receive an aspirating syringe 1 from the needle tip 3 to the body flange 5, either from the proximal end or from the partially open side of tubular member 2310. Further, tubular member 2310 has a diameter that is smaller than the diameter of body flange 5 of aspirating syringe 1 to prevent syringe 1 from falling into the interior cavity defined within tubular member 2310. Additionally, tubular member 2310 is of a diameter and length sufficient to receive metal body 4 of syringe 1. Tubular member 2310 has a length such that when body flange 5 rests upon the proximal open end of tubular member 2310, needle tip 3 is suspended above the bottom of tubular member 2310 and in addition, tubular member 2310 has a diameter large enough to receive a bent needle tip 3.

The foregoing embodiments have been presented for the purpose of illustration and description only and are not to be construed as limiting the scope of the invention in any way. The scope of the invention is to be determined from the claims appended hereto.

That which is claimed is:

1. An apparatus for the temporary storage and transport of sharps devices having an injury surface that causes a sharps injury or contamination, comprising:
    an elongate body, comprising:
        a first co-axial tubular member,
        a second co-axial tubular member, wherein the first co-axial tubular member defines a first interior cylindrical cavity and comprises a first proximal end, a first distal end and a proximal collar, wherein the second co-axial tubular member defines a second interior cylindrical cavity and comprises a second proximal end and a second distal end, where the outer diameter of second co-axial tubular member is smaller than the inner diameter of first interior cylindrical cavity, wherein further first co-axial tubular member is slideably disposed upon second co-axial tubular member so that first co-axial tubular member moves axially between a first proximal position to a second distal position toward the base, wherein proximal collar comprises an inner diameter smaller than the outer diameter of second co-axial tubular member thus restricting the axial movement of first co-axial tubular member towards the proximal face of the base, wherein further the second co-axial tubular member is fixed to the proximal face of the base at an angle to the proximate surface of the base, wherein further the first and second co-axial tubular members are maintained in a co-axial relationship, wherein further first and second co-axial tubular members each comprise complementary side openings configured to receive a sharps device into the second interior cylindrical cavity;
    a base, comprising:
        a proximal face;
        a distal face, the proximal face disposed at an angle to the distal face;
        a recess extending into the base from the proximal face; and
        a capture member disposably inserted within the recess, wherein a sharps device injury surface gripping material is disposed at the distal end of the capture member; and
    a compression spring disposed between the elongate body and the proximal face of the base.

2. The apparatus of claim 1, wherein the injury surface comprises a syringe needle, or a scalpel blade.

3. The apparatus of claim 2, wherein the sharps device comprises a syringe or a scalpel.

4. The apparatus of claim 3, wherein the sharps device injury surface gripping material comprises one or more of nylon, polyester or adhesive.

\* \* \* \* \*